United States Patent [19]

Morazzoni et al.

[11] Patent Number: 5,902,823
[45] Date of Patent: May 11, 1999

[54] METHOD FOR TREATING ADDICTION USING FORSKOLIN OR EXTRACTS CONTAINING FORSKOLIN

[75] Inventors: Paolo Morazzoni; Ezio Bombardelli, both of Milan, Italy

[73] Assignee: Indena S.p.A., Milan, Italy

[21] Appl. No.: 08/952,472

[22] PCT Filed: May 9, 1996

[86] PCT No.: PCT/EP96/01952

§ 371 Date: Nov. 17, 1997

§ 102(e) Date: Nov. 17, 1997

[87] PCT Pub. No.: WO96/36332

PCT Pub. Date: Nov. 21, 1996

[30] Foreign Application Priority Data

May 19, 1995 [IT] Italy .................................. MI95A1023

[51] Int. Cl.⁶ .......................... A61K 31/35; A61K 35/78
[52] U.S. Cl. .......................... 514/453; 514/455; 514/810; 514/811; 514/812
[58] Field of Search .................................... 514/453, 455, 514/810, 811, 812

[56] References Cited

U.S. PATENT DOCUMENTS

| | | | |
|---|---|---|---|
| 4,120,975 | 10/1978 | Orr et al. | 424/283 |
| 4,782,082 | 11/1988 | Kreutner et al. | 514/454 |
| 5,366,990 | 11/1994 | Reid | 514/397 |
| 5,371,104 | 12/1994 | Feigenbaum | 514/455 |

OTHER PUBLICATIONS

Szabó et al., Forskolin Promotes the Development of Ethanol Tolerance in 6–Hydroxydopamine–Treated Mice, Life Science, vol. 42, pp. 615–621 (1988).

*Primary Examiner*—Frederick Krass
*Attorney, Agent, or Firm*—Pennie & Edmonds LLP

[57] ABSTRACT

The present invention relates to the use of forskolin and of the extracts containing it for the treatment of alcohol addiction.

5 Claims, 1 Drawing Sheet

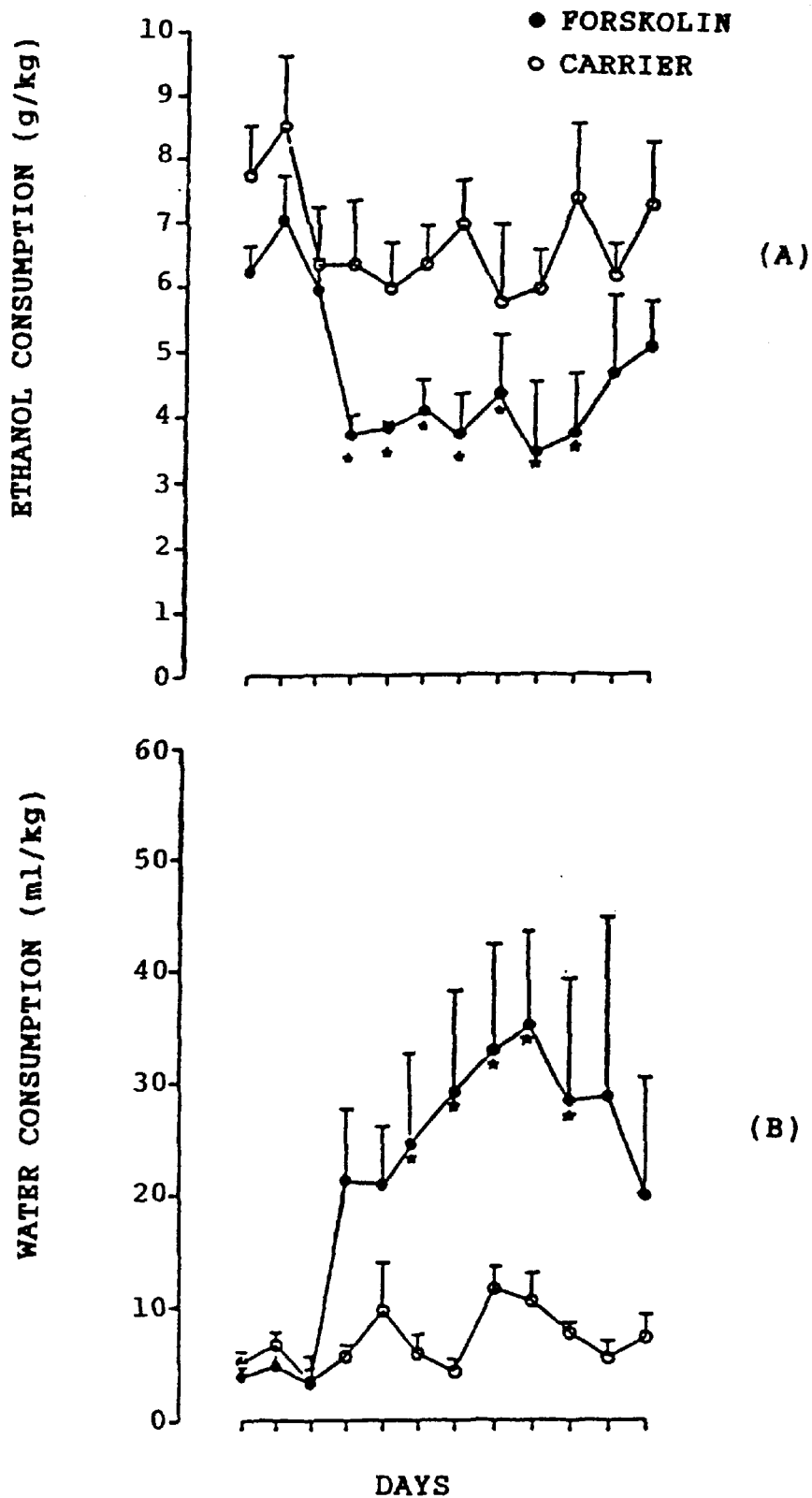
Fig. 1 – Effect of the repeated oral administration of forskolin (50 mg/kg) on alcohol (A) and water (B) consumption in sP (Sardinian alcohol-preferring) rats.

METHOD FOR TREATING ADDICTION USING FORSKOLIN OR EXTRACTS CONTAINING FORSKOLIN

BACKGROUND OF THE INVENTION

The present invention relates to pharmaceutical compositions for the treatment of alcohol addiction, characterized in that they contain—as the active principle—forskolin or extracts containing it.

Alcohol abuse and alcohol addiction, phenomena which can be collectively referred to by the term alcoholism, represent a serious problem for the whole of modern society (Gessa G. L., Bisogno compulsivo di bere e "principio del piacere" [The compulsive need to drink and the pleasure principle] in Medicina delle tossicodipendenze [Drug Addiction Medicine] II, 5 (1994)). In Italy, for example, more than 9% of the population (about 5 million people) are heavy drinkers and more than 1 million people are alcohol-addict (Calamo-Specchia F. P.—Epidemiologia dell'alcolismo in Italia [Epidemiology of alcoholism in Italy] in Atti del VII Congresso Nazionale della S.I.A., [Records of the 7th National Congress of the S.I.A.] Mediserve, Rome, 295–301, (1991)). These figures become much higher if we consider countries such as the United States of America where there are more than 13 million alcohol-addicts. Alcohol abuse and actual alcohol addiction result in an enormous outlay of public money (recently, since 1991, in the United States about 200 thousand million dollars a year have been spent) and are the cause of enormous social and psychological damage for the individuals involved.

The existing approaches for the treatment of alcoholism, in addition to those of a psychological nature (group therapy, etc.), consist in the use of drugs such as disulfiram and calcium carbamide which act on the metabolism of alcohol, inhibiting hepatic aldehyde-dehydrogenase and therefore raising the hematic levels of acetaldehyde, with all the undesiderable phenomena which occur each time ethanol is taken.

According to the present state of the art, the sole plant whose derivatives have been used for the treatment of alcoholism is the Pueraria lobata (Radix puerarie), which is widely used in traditional Chinese medicine and forms the subject of Patent Application WO 93/00896.

SUMMARY OF THE INVENTION

It has now been surprisingly found that forskolin can be used with success for reducing the voluntary consumption of alcohol and other drugs which induce addiction.

BRIEF DESCRIPTION OF THE DRAWINGS

FIG. 1(a) and 1(b) is a graph showing the effect of treatment on alcohol and water consumption.

DETAILED DESCRIPTION OF THE INVENTION

Forskolin, i.e. 17-β-acetoxy-8,13-epoxy-1α, 6β, 9α-trihydroxylabd-14-en-11-one, of formula:

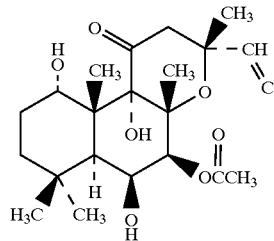

is a diterpenoid isolated from the plant Coleus forskohlii, native to India, which is capable of activating adenylate cyclase.

Its pharmacological activity is described by De Souza and Shah in Economic and Medicinal Plant Research vol. 2, H. Wagner, H. Hihino and N. Farusuworth ed., Academic Press. 1988.

The uses of forskolin in the treatment of cardiocirculatory and respiratory diseases and of glaucoma are known; for a review see, for example, the above cited reference; Seamon and Daly, Adv. Cyclic Nucleotide Res. 20, 1.

Determination of the inhibiting action on alcohol consumption was performed using alcohol-consuming rats of the strain called "Sardinian alcohol-preferring" (Sp) (Fadda P., Mosca E., Colombo G., Gessa G. L., Alcohol—preferrinq rats: Genetic sensitivity to alcohol—induced stimulation of dopamine metabolism, in Physiol. Behav. 47, 727 (1990)).

These animals, which given a free choice between alcohol and water consume daily 6 to 7 g of alcohol per kg of body weight (with a water-to-alcohol ratio higher than 2:1), during the last few years have been used with success to determine the effect of various substances on the voluntary consumption of alcohol; see, for example, Balakleevsky A., Colombo G., Fadda F., Gessa G. L., Ro 19-4603, a benzodiazepine receptor inverse agonist, attenuates voluntary ethanol consumption in rats selectively bred for hiah ethanol preference, in Alcohol Alcohol. 25, 449–452 (1990); Fadda F., Garau B., Colombo G., Gessa G. L., Isradipine and other calcium channel antagonists attenuate ethanol consumption in ethanol—preferring rats, in Alcoholism: Clinical and Experimental Research 16(3), 449–452 (1992).

The animals, which were kept under normal housing conditions, were given a free choice between water (which was always present) and alcohol (a 10% solution v/v) which was offered for a period of 4 hours a day (i.e. the first 4 hours of darkness during the day/night cycle). The amounts of water and alcohol consumed were recorded every day at the same time. Food was offered ad libitum. Once a stable consumption of alcohol and water was reached, forskolin at a dosage of 50 mg/kg, dissolved in dimethylsulfoxide, was administered orally in a volume amount of 2 ml/kg once a day for 7 consecutive days. An equal volume of the carrier was used as the control. At the end of treatment, the alcohol and water consumption was recorded until the values recorded prior to the treatment were re-established.

FIG. 1A shows the effect of repeated oral administration of 50 mg/kg of forskolin on alcohol consumption; FIG. 1B shows the effect on water consumption.

From an examination of FIG. 1 it can be concluded that forskolin reduces alcohol consumption significantly. The reduction in alcohol consumption remains constant until the seventh day and then regresses following suspension of the treatment. Moreover, it is surprising to note that this trend is accompanied by the tendency for a gradual increase in the water consumption, as if the animal were substituting it for the alcohol. This latter observation is of particular importance since it shows that the treatment carried out with the product being tested is perfectly well-tolerated and the animal returns without any difficulty to a more physiological life cycle, using water instead of alcohol.

The invention therefore provides pharmaceutical compositions which can be administered orally and which contain as the active principle forskolin. The compositions of the invention, in addition to conventional excipients or carriers, will contain from about 10 to about 500 mg of the active principle.

EXAMPLE 1
Sachet formulation
Each 2,300 mg sachet contains:
Forskolin 100 mg
Saccharose 2,000 mg
Maltodextrin 110 mg
Citric acid 30 mg
Orange flavor 40 mg
Hydrogenated vegetable oils 20 mg

EXAMPLE 2
Tablet formulation
Each 100 mg tablet contains:
Forskolin 25 mg
Microcrystalline cellulose 25 mg
Lactose 37 mg
Colloidal silica 1 mg
Cross-linked sodium carboxymethylcellulose 6 mg
Polyvinylpyrrolidone 5 mg
Magnesium stearate 1 mg

I claim:

1. A method for the treatment of a patient suffering from alcohol addiction, comprising administering to said patient a pharmaceutical composition comprising a therapeutically effective amount of forskolin or an extract containing forskolin in a pharmaceutically acceptable carrier.

2. A method according to claim 1 wherein said composition is administered orally.

3. A method according to claim 1 wherein the amount administered is a dosage of about 10 to about 500 mg of forskolin.

4. A method according to claim 3 wherein said dosage is formulated as a tablet.

5. A method according to claim 3 wherein said dosage is formulated as a sachet.

* * * * *

UNITED STATES PATENT AND TRADEMARK OFFICE
CERTIFICATE OF CORRECTION

PATENT NO. : 5,902,823

DATED : May 11, 1999

INVENTORS : Paolo Morazzoni et al.

It is certified that error appears in the above-identified patent and that said Letters Patent is hereby corrected as shown below: On the title page: Item [54] and Col. 1, line 3, after "TREATING" insert --ALCOHOL--.

Signed and Sealed this

Twelfth Day of October, 1999

Attest:

Q. TODD DICKINSON

Attesting Officer

Acting Commissioner of Patents and Trademarks